United States Patent
Pham et al.

(10) Patent No.: US 6,858,571 B2
(45) Date of Patent: Feb. 22, 2005

(54) PENTAFLUOROPROPENE-BASED COMPOSITIONS

(75) Inventors: Hang T. Pham, Amherst, NY (US); Rajiv R. Singh, Getzville, NY (US); David P. Wilson, East Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/694,079

(22) Filed: Oct. 27, 2003

(65) Prior Publication Data

US 2004/0127383 A1 Jul. 1, 2004

Related U.S. Application Data

(60) Provisional application No. 60/421,435, filed on Oct. 25, 2002, and provisional application No. 60/421,263, filed on Oct. 25, 2002.

(51) Int. Cl.$^7$ .......................... C07C 19/08; C23G 5/028
(52) U.S. Cl. ..................... 510/408; 510/411; 252/67; 252/364; 62/114
(58) Field of Search .................. 252/67, 364; 510/408, 510/177, 411; 134/40, 10

(56) References Cited

U.S. PATENT DOCUMENTS

| | | | | | |
|---|---|---|---|---|---|
| 5,396,000 | A | * | 3/1995 | Nappa et al. ............... | 570/175 |
| 5,679,875 | A | * | 10/1997 | Aoyama et al. ............. | 570/156 |
| 6,176,102 | B1 | * | 1/2001 | Novak et al. ................ | 62/612 |
| 6,376,727 | B1 | * | 4/2002 | Rao et al. ................... | 570/157 |
| 6,548,720 | B2 | * | 4/2003 | Manogue et al. ............ | 570/157 |
| 2002/0002314 | A1 | * | 1/2002 | Qian et al. .................. | 570/155 |
| 2002/0115895 | A1 | * | 8/2002 | Manogue et al. ............ | 570/156 |
| 2003/0042463 | A1 | * | 3/2003 | Arman et al. ................ | 252/67 |

OTHER PUBLICATIONS

Downing, Ralph C., "Fluorocarbon Refrigerants Handbook," *Prentice Hall*, Chapter 3 (1988).

Saunders and Frisch, "Polyurethanes Chemistry and Technology," vols. I and II, John Wiley & Sons, New York, NY (1962).

Swietoslaski, W. "Ebulliometric Measurements", Reinhold Publishing Corporation, New York, NY (1945).

* cited by examiner

*Primary Examiner*—Gregory Webb
(74) *Attorney, Agent, or Firm*—Colleen D. Szuch

(57) ABSTRACT

Provided are azeotrope-like compositions comprising pentafluoropropene (HFO-1225) and a fluid selected from the group consisting of 3,3,3-trifluoropropene ("HFO-1243zf"), 1,1-difluoroethane ("HFC-152a"), trans-1,3,3,3-tetrafluoropropene ("HFO-1234ze"), and combinations of two or more thereof. Also provided are uses thereof including as refrigerants, blowing agents, sprayable compositions, flame suppressant, and the like.

72 Claims, No Drawings

PENTAFLUOROPROPENE-BASED COMPOSITIONS

CROSS-REFERENCE TO RELATED APPLICATIONS

This application is related to and claims the priority benefit to U.S. Provisional Application Ser. Nos. 60/421,435 and 60/421,263, each of which was filed with the United States Patent and Trademark Office on Oct. 25, 2002, and each of which is incorporated herein by reference. The present application is also related to and incorporates by reference each of the following concurrently filed U.S. patent applications: Ser. No. 10/695,212 entitled "Fluorinated Alkene Refrigerant Composition," by Raymond Thomas and Ser. No. 10/694,272 entitled "Process For Producing Fluoropropenes," by Hsueh Sung Tung et al.

FIELD OF THE INVENTION

The present invention relates generally to compositions of pentafluoropropene. More specifically, the present invention provides azeotrope-like compositions comprising pentafluoropropene and uses thereof.

BACKGROUND

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, it is desirable to use fluids having low or even zero ozone depletion potential, such as hydrofluorocarbons ("HFC's"). Thus, the use of fluids that do not contain chlorofluorocarbons ("CFCs") or hydrochlorofluorocarbons ("HCFCs") is desirable. Additionally, the use of single component fluids or azeotropic mixtures, which do not fractionate on boiling and evaporation, is desirable. However, the identification of new, environmentally-safe, non-fractionating mixtures is complicated due to the fact that azeotrope formation is not readily predictable.

The industry is continually seeking new fluorocarbon based mixtures that offer alternatives, and are considered environmentally safer substitutes for CFCs and HCFCs. Of particular interest are mixtures containing hydrofluorocarbons of low ozone depletion/low global warming potentials. Such mixtures are the subject of this invention.

DESCRIPTION OF PREFERRED EMBODIMENTS

The present inventors have developed compositions that can help to satisfy the continuing need for substitutes for CFCs and HCFCs. In certain embodiments, the present invention provides azeotrope-like compositions comprising, or consisting essentially of, pentafluoropropene ("HFO-1225"), and a fluid selected from the group consisting of 3,3,3-trifluoropropene ("HFO-1243zf"), 1,1-difluoroethane ("HFC-152a"), trans-1,3,3,3-tetrafluoropropene ("HFO-1234ze"), and combinations of two or more thereof. Thus, the present invention overcomes the aforementioned shortcomings by providing azeotrope-like compositions that are substantially free of CFCs and HCFCs and which exhibit relatively constant boiling point and vapor pressure characteristics.

As used herein, the term "HFO-1225" for pentafluoropropene refers to, and encompasses, all isomers of pentafluoropropene, including, for example, the E- and Z-isomers of 1,1,1,2,3-pentafluoropropene ("HFO-1225ye"), as well as, 1,1,1,3,3-pentafluoropropene ("HFO-1225zc") and 1,1,2,3,3-pentafluoropropene ("HFO-1225yc").

As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant-boiling and cannot be separated during a phase change.

Azeotrope-like compositions are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotrope-like compositions of the invention within the indicated ranges as well as certain compositions outside these ranges are azeotrope-like.

The azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

According to certain preferred embodiments, the present invention provides an azeotrope-like composition comprising, preferably consisting essentially of, HFO-1225 and a fluid selected from the group consisting of HFO-1243zf, HFC-152a, HFO-1234ze, and combinations of two or more thereof. Preferably, such azeotrope-like compositions comprise, preferably consist essentially of, from greater than zero to about 99 wt. % of HFO-1225 and from about 1 wt. % to less than 100 wt. % of the fluid selected from the group consisting of HFO-1243zf, HFC-152a, HFO-1234ze, and combinations of two or more thereof. More preferably, the present azeotrope-like compositions comprise, and preferably consist essentially of, from about 5 wt. % to about 90 wt. % of HFO-1225 and from about 10 wt. % to about 95 wt. % of the fluid selected from the group consisting of HFO-1243zf, HFC-152a, HFO-1234ze, and combinations of two or more thereof. Other preferred compositions comprise, or consist essentially of, greater than zero to about 75 wt. % of HFO-1225 and from about 25 wt. % to less than 100 wt. % of the fluid selected from the group consisting of HFO-1243zf, HFC-152a, HFO-1234ze, and combinations of two or more thereof. Certain other preferred compositions of the present invention comprise from greater than zero to about 20 wt. % of HFO-1225 and from about 80 wt. % to less than 100 wt. % of the fluid selected from the group consisting of HFO-1243zf, HFC-152a, HFO-1234ze, and combinations of two or more thereof. Other preferred compositions of the present invention from about 40 wt. % to about 90 wt. % of HFO-1225 and from about 10 wt. % to about 60 wt. % of the fluid selected from the group consisting of HFO-1243zf, HFC-152a, HFO-1234ze, and combinations of two or more thereof. Unless otherwise indicated, all weight percents reported herein are based on the total weight of the HFO-1225 and fluid selected from the group consisting of 3,3,3-trifluoropropene ("HFO-1243zf"), 1,1-difluoroethane ("HFC-152a"), trans-1,3,3,3-tetrafluoropropene ("HFO-1234ze"), and combinations of two or more thereof, in the azeotrope-like composition.

According to certain preferred embodiments, the present HFO-1225 azeotrope-like compositions have a boiling point of from about –18!C to about –28° C., more preferably, –22° C. to about –28° C., and more preferably about –23° C. to about –27° C., at about 14 psia. In certain other preferred embodiments, the present compositions have a boiling point of about –20° C.±2° C., more preferably –20° C.±1° C. Additionally, in certain preferred embodiments the HFO-1225 compositions of the present invention are substantially homogenous azeotrope-like compositions.

HFO-1225/HFO-1243zf

Certain preferred embodiments of the present invention provide azeotrope-like compositions comprising HFO-1225 and HFO-1243zf. Preferably, the novel azeotrope-like compositions of the present invention comprise effective amounts of HFO-1225 and HFO-1243zf. The term "effective amounts" as used herein refers to the amount of each component which upon combination with the other component or components, results in the formation of the present azeotrope-like compositions. These embodiments preferably provide azeotrope-like compositions comprising, and preferably consisting essentially of, from greater than zero to about 50 weight percent HFO-1225 and from about 50 wt. % to less than 100 wt. % HFO-1243zf, preferably from greater than zero to about 25 wt. % HFO-1225 and from about 75 wt. % to less than 100 wt. % HFO-1243zf, and more preferably from about 1 to about 20 wt. % HFO-1225 and from about 80 to about 99 wt. % HFO-1243zf.

Preferably, the HFO-1225/HFO-1243zf compositions of the present invention have a boiling of about –25° C.±3°° C. at about 14 psia. In certain embodiments, the compositions have a boiling point of preferably about –25° C.±2° C. at about 14 psia.

Certain preferred HFO-1225/HFO-1243zf compositions of the present invention comprise azeotrope-like compositions comprising, or consisting essentially of, effective amounts of HFO-1225ye (either E-isomer "E-HFO-1225ye", Z-isomer "Z-HFO-1225ye", or a combination thereof "E/Z-HFO-1225ye") and HFO-1243zf. Such embodiments preferably provide azeotrope-like compositions comprising, and preferably consisting essentially of, from greater than zero to about 50 weight percent HFO-1225ye and from about 50 wt. % to less than 100 wt. % HFO-1243zf, preferably from greater than zero to about 25 wt. % HFO-1225ye and from about 75 wt. % to less than 100 wt. % HFO-1243zf, more preferably from about 1 to about 20 wt. % HFO-1225ye and from about 80 to about 99 wt. % HFO-1243zf, and even more preferably from about 1 to about 15 wt. % HFO-1225ye and from about 85 to about 99 wt. % HFO-1243zf.

In certain preferred embodiments, the HFO-1225ye/HFO-1243zf compositions of the present invention comprise, or consist essentially of, Z-HFO-1225ye and HFO-1243zf or E/Z-HFO-1225ye and HFO-1243zf. In certain more preferred embodiments the present HFO-1225ye/HFO-1243zf compositions comprise, or consist essentially of, Z-HFO-1225ye and HFO-1243zf.

Preferably, the HFO-1225ye/HFO-1243zf compositions of the present invention have a boiling of from about –24° C. to about –28° C., preferably from about –25° C. to about –28° C., and even more preferably from about –26° C. to about –28° C. at about 14.4 psia.

Certain other preferred HFO-1225/HFO-1243zf compositions of the present invention comprise azeotrope-like compositions comprising, or consisting essentially of, effective amounts of HFO-1225zc and HFO-1243zf. Such embodiments preferably provide azeotrope-like compositions comprising, and preferably consisting essentially of, from greater than zero to about 50 weight percent HFO-1225zc and from about 50 wt. % to less than 100 wt. % HFO-1243zf, preferably from greater than zero to about 40 wt. % HFO-1225zc and from about 60 wt. % to less than 100 wt. % HFO-1243zf, more preferably from about 1 to about 20 wt. % HFO-1225zc and from about 80 to about 99 wt. % HFO-1243zf, and even more preferably from about 3 to about 20 wt. % HFO-1225zc and from about 80 to about 97 wt. % HFO-1243zf.

Preferably, the HFO-1225zc/HFO-1243zf compositions of the present invention have a boiling of from about –23° C. to about –27° C., preferably from about –23° C. to about –26° C., and even more preferably from about –24° C. to about –26° C. at about 14 psia.

HFO-1225/HFC-152a

In certain other preferred embodiments, the present invention provides azeotrope-like compositions comprising HFO-1225 and HFC-152a. Preferably, such novel azeotrope-like compositions of the present invention comprise, or consist essentially of, effective amounts of HFO-1225 and HFC-152a. These embodiments preferably provide azeotrope-like compositions comprising, and preferably consisting essentially of, from greater than zero to about 99 weight percent HFO-1225 and from about 1 wt. % to less than 100 wt. % HFC-152a, more preferably from greater than zero to about 75 wt. % HFO-1225 and from about 25 wt. % to less than 100 wt. % HFC-152a, even more preferably from about 2 wt. % to about 60 wt. % HFO-1225 and from about 40 to about 98 wt. % HFC-152a. Other preferred compositions comprise, or consist essentially of, from about 5 wt. % to about 90 wt. % HFO-1225 and from about 10 to about 95 wt. % HFC-152a.

Preferably, the HFO-1225/HFC-152a compositions of the present invention have a boiling of about –21° C. to about –26° C., at about 14 psia.

Certain preferred HFO-1225/HFC-152a compositions of the present invention comprise azeotrope-like compositions comprising, or consisting essentially of, effective amounts of HFO-1225ye (E, Z, or E/Z) and HFC-152a. Such embodiments preferably provide azeotrope-like compositions comprising, and preferably consisting essentially of, from greater than zero to about 75 weight percent HFO-1225ye and from about 25 wt. % to less than 100 wt. % HFC-152a, more preferably from greater than zero to about 60 weight percent HFO-1225ye and from about 40 wt. % to less than 100 wt. % HFC-152a, even more preferably from greater than zero to about 40 weight percent HFO-1225ye and from about 60 wt. % to less than 100 wt. % HFC-152a, and even more preferably from about 1 to about 25 weight percent HFO-1225ye and from about 75 wt. % to about 99 wt. % HFC-152a.

In certain preferred embodiments, the HFO-1225ye/HFC-152a compositions of the present invention comprise, or consist essentially of, Z-HFO-1225ye and HFC-152a or E/Z-HFO-1225ye and HFC-152a. In certain more preferred embodiments the present HFO-1225ye/HFC-152a compositions comprise, or consist essentially of, Z-HFO-1225ye and HFC-152a.

Preferably, the HFO-1225ye/HFC-152a compositions of the present invention have a boiling of about $-23°$ C.$\pm2°$ C., preferably $-23°$ C.$\pm1°$ C. at about 14 psia.

The present invention provides certain other preferred azeotrope-like compositions comprising HFO-1225zc and HFC-152a. Such compositions preferably comprise, or consist essentially of, from greater than zero to about 99 weight percent HFO-1225zc and from about 1 wt. % to less than 100 wt. % HFC-152a, more preferably from about 10 wt. % to about 99 wt. % HFO-1225zc and from about 1 wt. % to about 90 wt. % HFC-152a, even more preferably from about 10 wt. % to about 60 wt. % HFO-1225zc and from about 90 wt. % to about 40 wt. % HFC-152a, and even more preferably from about 10 wt. % to about 50 wt. % HFO-1225zc and from about 90 wt. % to about 50 wt. % HFC-152a.

Preferably, the HFO-1225zc/HFC-152a compositions of the present invention have a boiling of about $-24°$ C.$\pm2°$ C., and preferably about $-24°$ C.$\pm1°$ C., at about 14 psia.

HFO-1225/HFO-1234ze

In certain other preferred embodiments, the present invention provides azeotrope-like compositions comprising HFO-1225 and HFO-1234ze. Preferably, such novel azeotrope-like compositions of the present invention comprise, or consist essentially of, effective amounts of HFO-1225 and HFO-1234ze. These embodiments preferably provide azeotrope-like compositions comprising, and preferably consisting essentially of, from about 1 wt. % to 99 wt. % HFO-1225 and from about 1 wt. % to 99 wt. % HFO-1234ze, more preferably from about 25 wt. % to about 99 wt. % HFO-1225 and from 1 to about 75 wt. % HFO-1234ze, even more preferably from about 30 wt. % to about 90 wt. % HFO-1225 and from about 10 to about 70 wt. % HFO-1234ze, and even more preferably from about 50 wt. % to about 90 wt. % HFO-1225 and from about 10 to about 50 wt. % HFO-1234ze.

Preferably, the HFO-1225/HFO-1234ze compositions of the present invention have a boiling of about $-20°$ C.$\pm2°$ C., and preferably about $-20°$ C.$\pm1°$ C. at about 14.40 psia.

Certain preferred HFO-1225/HFO-1234ze compositions of the present invention comprise azeotrope-like compositions comprising, or consisting essentially of, effective amounts of HFO-1225ye (E, Z, or E/Z—isomer(s)) and HFO-1234ze. Such embodiments preferably provide azeotrope-like compositions comprising, and preferably consisting essentially of, from about 1 wt. % to 99 wt. % HFO-1225ye and from about 1 wt. % to 99 wt. % HFO-1234ze, more preferably from about 25 wt. % to about 99 wt. % HFO-1225ye and from 1 to about 75 wt. % HFO-1234ze, even more preferably from about 30 wt. % to about 90 wt. % HFO-1225ye and from about 10 to about 70 wt. % HFO-1234ze, and even more preferably from about 50 wt. % to about 90 wt. % HFO-1225ye and from about 10 to about 50 wt. % HFO-1234ze.

In certain preferred embodiments, the HFO-1225ye/HFO-1234ze compositions of the present invention comprise, or consist essentially of, Z-HFO-1225ye and HFO-1234ze or E/Z-HFO-1225ye and HFO-1234ze. In certain more preferred embodiments the present HFO-1225ye/HFO-1234ze compositions comprise, or consist essentially of, Z-HFO-1225ye and HFO-1234ze.

Preferably, the HFO-1225ye/HFO-1234ze compositions of the present invention have a boiling of about $-20°$ C.$\pm2°$ C., and preferably about $-20°$ C.$\pm1°$ C. at about 14.40 psia.

Uses of the Compositions

The present compositions have utility in a wide range of applications. For example, one embodiment of the present invention relates to refrigerant compositions comprising the present azeotrope-like compositions.

The refrigerant compositions of the present invention may be used in any of a wide variety of refrigeration systems including air-conditioning, refrigeration, heat-pump, HVAC systems, and the like. The preferred compositions of the present invention tend to exhibit many of the desirable characteristics of HFC refrigerants, including a GWP that is much lower than that of conventional HFC refrigerants and a compressor discharge temperature that is as low or lower than such refrigerants. In addition, the relatively constant boiling nature of the compositions of the present invention makes them even more desirable than certain conventional HFCs for use as refrigerants in many applications.

According to certain other embodiments, the present invention provides refrigeration systems comprising a refrigerant of the present invention and methods of producing heating or cooling by condensing and/or evaporating a composition of the present invention. In certain preferred embodiments, the methods for cooling an article according to the present invention comprise evaporating a refrigerant composition comprising an azeotrope-like composition of the present invention in the vicinity of the article to be cooled. Certain preferred methods for heating an article comprise condensing a refrigerant composition comprising an azeotrope-like composition of the present invention in the vicinity of the article to be heated. In light of the disclosure herein, those of skill in the art will be readily able to heat and cool articles according to the present inventions without undue experimentation.

In another embodiment, the azeotrope-like compositions of this invention may be used as propellants in sprayable compositions, either alone or in combination with known propellants. The propellant composition comprises, more preferably consists essentially of, and, even more preferably, consists of the azeotrope-like compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as deodorants, perfumes, hair sprays, cleansers, and polishing agents as well as medicinal materials such as anti-asthma and anti-halitosis medications.

Yet another embodiment of the present invention relates to a blowing agent comprising one or more azeotrope-like compositions of the invention. In other embodiments, the invention provides foam premixes, foamable compositions, and preferably polyurethane, polyisocyanurate and thermoplastic foam compositions, and methods of preparing foams. In such foam embodiments, one or more of the present azeotrope-like compositions are included as a blowing agent in a foamable composition, which composition preferably includes one or more additional components capable of reacting and/or foaming under the proper conditions to form a foam or cellular structure, as is well known in the art. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention.

In addition, according to certain embodiments, the blowing agents of the present invention are used to blow thermoplastic foams, such as polystyrene and polyethylene foams, including low-density polyethylene foams. Any of a wide range of conventional methods for blowing such thermoplastic foams can be adapted for use herein.

According to certain other preferred embodiments, the present invention provides methods for reducing the flammability of a fluid, said methods comprising adding an azeotrope-like composition of the present invention to said fluid. The flammability associated with any of a wide range of flammable fluids may be reduced according to the present invention. For example, the flammability associated with fluids such as ethylene oxide, flammable hydrofluorocarbons and hydrocarbons, including: HFC-152a, 1,1,1-trifluoroethane (HFC-143a), difluoromethane (HFC-32), propane, hexane, octane, and the like can be reduced according to the present invention. For the purposes of the present invention, a flammable fluid may be any fluid exhibiting flammability ranges in air as measured via any standard conventional test method, such as ASTM E-681, and the like.

Any suitable amounts of a present azeotrope-like composition may be added to reduce flammability of a fluid according to the present invention. As will be recognized by those of skill in the art, the amount added will depend, at least in part, on the degree to which the subject fluid is flammable and the degree to which it is desired to reduce the flammability thereof. In certain preferred embodiments, the amount of azeotrope-like composition added to the flammable fluid is effective to render the resulting fluid non-flammable.

The present invention further provides methods of suppressing a flame, said methods comprising contacting a flame with a fluid comprising an azeotrope-like composition of the present invention. Any suitable methods for contacting the flame with the present composition may be used. For example, an azeotrope-like composition of the present invention may be sprayed, poured, and the like onto the flame, or at least a portion of the flame may be immersed in the azeotrope-like composition. In light of the teachings herein, those of skill in the art will be readily able to adapt a variety of conventional apparatus and methods of flame suppression for use in the present invention.

Furthermore, many articles, devices and materials, particularly for use in the medical field, must be sterilized prior to use for the health and safety reasons, such as the health and safety of patients and hospital staff. The present invention provides methods of sterilizing comprising contacting the articles, devices or material to be stearilized with a compound or composition of the present invention. Such methods may be either high or low-temperature sterilization methods. In certain embodiments, high-temperature sterilization comprises exposing the articles, device or material to be sterilized to a hot fluid comprising a compound or composition of the present invention at a temperature of from about 250 to about 270° F., preferably in a substantially sealed chamber. The process can be completed usually in less than about 2 hours. However, some articles, such as plastic articles and electrical components, cannot withstand such high temperatures and require low-temperature sterilization.

Low-temperature sterilization of the present invention involves the use of a compound or composition of the present invention at a temperature of from about 100 to about 200° F. The compounds of the present invention may be combined with other common chemical sterilants, including, for example, ethylene oxide (EO), formaldehyde, hydrogen peroxide, chlorine dioxide, and ozone to form a sterilant composition of the present invention.

The low-temperature sterilization of the present invention is preferably at least a two-step process performed in a substantially sealed, preferably air tight, chamber. In the first step (the sterilization step), the articles having been cleaned and wrapped in gas permeable bags are placed in the chamber. Air is then evacuated from the chamber by pulling a vacuum and perhaps by displacing the air with steam. In certain embodiments, it is preferable to inject steam into the chamber to achieve a relative humidity that ranges preferably from about 30% to about 70%. Such humidities may maximize the sterilizing effectiveness of the sterilant which is introduced into the chamber after the desired relative humidity is achieved. After a period of time sufficient for the sterilant to permeate the wrapping and reach the interstices of the article, the sterilant and steam are evacuated from the chamber.

In the preferred second step of the process (the aeration step), the articles are aerated to remove sterilant residues. Removing such residues is particularly important in the case of toxic sterilants, although it is optional in those cases in which the substantially non-toxic compounds of the present invention are used. Typical aeration processes include air washes, continuous aeration, and a combination of the two. An air wash is a batch process and usually comprises evacuating the chamber for a relatively short period, for example, 12 minutes, and then introducing air at atmospheric pressure or higher into the chamber. This cycle is repeated any number of times until the desired removal of sterilant is achieved. Continuous aeration typically involves introducing air through an inlet at one side of the chamber and then drawing it out through an outlet on the other side of the chamber by applying a slight vacuum to the outlet. Frequently, the two approaches are combined. For example, a common approach involves performing air washes and then an aeration cycle.

Other uses of the present azeotrope-like compositions include use as solvents, cleaning agents, and the like. Those of skill in the art will be readily able to adapt the present compositions for use in such applications without undue experimentation.

EXAMPLES

The invention is further illustrated in the following examples which are intended to be illustrative, but not limiting in any manner.

For examples 1–15 and ebulliometer as described by Swietolslowski in his book "Ebulliometric Measurements" (Reinhold, 1945) was used.

Example 1

An ebulliometer, as described above, consisting of a vacuum jacketed tube with a condenser on top which is further equipped with a quartz thermometer is used. About 26 g HFO-1243zf is charged to the ebulliometer and then Z-HFO-1225ye is added in small, measured increments. Temperature depression is observed when Z-HFO-1225ye is added to the HFO-1243zf, indicating a minimum boiling azeotrope is formed. As shown in Table 1, from greater than about 0 to about 25 weight percent Z-HFO-1225ye, the boiling point of the composition changed by about 1° C. or less.

TABLE 1

Z-HFO-1225ye/HFO-1243zf compositions at 14.40 psia

| Wt. % HFO-1243zf | Wt. % Z-HFO-1225ye | Temperature (° C.) |
|---|---|---|
| 100.00 | 0.00 | −27.151 |
| 99.36 | 0.64 | −27.201 |
| 99.04 | 0.96 | −27.251 |
| 94.16 | 5.84 | −27.281 |
| 89.49 | 10.51 | −27.400 |
| 82.05 | 17.95 | −26.254 |
| 78.14 | 21.86 | −26.005 |
| 75.65 | 24.35 | −25.855 |

Example 2

An ebulliometer, as described above, consisting of a vacuum jacketed tube with a condenser on top which is further equipped with a quartz thermometer is used. About 26 g HFO-1243zf is charged to the ebulliometer and then E-HFO-1225ye is added in small, measured increments. Temperature depression is observed when E-HFO-1225ye is added to the HFO-1243zf, indicating a minimum boiling azeotrope is formed.

Example 3

An ebulliometer, as described above, consisting of a vacuum jacketed tube with a condenser on top which is further equipped with a quartz thermometer is used. About 26 g HFO-1243zf is charged to the ebulliometer and then E/Z-HFO-1225ye is added in small, measured increments. Temperature depression is observed when E/Z-HFO-1225ye is added to the HFO-1243zf, indicating a minimum boiling azeotrope is formed.

Example 4

An ebulliometer, as described above, consisting of a vacuum jacketed tube with a condenser on top which is further equipped with a quartz thermometer is used. About 18 g HFO-1243zf is charged to the ebulliometer and then HFO-1225zc is added in small, measured increments. Temperature depression is observed when HFO-1225zc is added to the HFO-1243zf, indicating a minimum boiling azeotrope is formed. As shown in Table 2, from greater than about 0 to about 40 weight percent HFO-1225zc, the boiling point of the composition changed by about 1° C. or less.

TABLE 2

HFO-1225zc/HFO-1243zf compositions at 14.34 psia

| Wt. % HFO-1243zf | Wt. % HFO-1225zc | Temperature (° C.) |
|---|---|---|
| 100.00 | 0.00 | −24.95 |
| 96.40 | 3.60 | −25.03 |
| 90.66 | 9.34 | −25.10 |
| 86.43 | 13.57 | −25.12 |
| 81.39 | 18.61 | −25.14 |
| 77.53 | 22.47 | −25.03 |
| 71.01 | 28.99 | −24.97 |
| 65.99 | 34.01 | −24.91 |
| 60.89 | 39.11 | −24.67 |

Example 5

An ebulliometer, as described above, consisting of a vacuum jacketed tube with a condenser on top which is further equipped with a quartz thermometer is used. About 26 g HFO-1243zf is charged to the ebulliometer and then HFO-1225yc is added in small, measured increments. Temperature depression is observed when HFO-1225yc is added to the HFO-1243zf, indicating a minimum boiling azeotrope is formed.

Example 6

An ebulliometer, as described above, consisting of a vacuum jacketed tube with a condenser on top which is further equipped with a quartz thermometer is used. About 15 g HFC-152a is charged to the ebulliometer and then Z-HFO-1225ye is added in small, measured increments. Temperature depression is observed when Z-HFO-1225ye is added to the HFC-152a, indicating a minimum boiling azeotrope is formed. As shown in Table 3, from greater than zero to about 53 weight percent Z-HFO-1225ye, the boiling point of the composition changed by about 1° C. or less.

TABLE 3

Z-HFO-1225ye/HFC-152a compositions at 14.44 psia

| Wt. % HFC-152a | Wt. % Z-HFO-1225ye | Temperature (° C.) |
|---|---|---|
| 100.00 | 0.00 | −23.441 |
| 98.02 | 1.98 | −23.470 |
| 92.88 | 7.12 | −23.745 |
| 82.29 | 17.71 | −23.745 |
| 76.96 | 23.04 | −23.666 |
| 69.61 | 30.39 | −23.637 |
| 62.33 | 37.67 | −23.558 |
| 55.57 | 44.43 | −23.509 |
| 46.96 | 53.04 | −23.313 |

Example 7

An ebulliometer, as described above, consisting of a vacuum jacketed tube with a condenser on top which is further equipped with a quartz thermometer is used. About 15 g HFC-152a is charged to the ebulliometer and then E-HFO-1225ye is added in small, measured increments. Temperature depression is observed when E-HFO-1225ye is added to the HFC-152a, indicating a minimum boiling azeotrope is formed.

Example 8

An ebulliometer, as described above, consisting of a vacuum jacketed tube with a condenser on top which is further equipped with a quartz thermometer is used. About 15 g HFC-152a is charged to the ebulliometer and then E/Z-HFO-1225ye is added in small, measured increments. Temperature depression is observed when E/Z-HFO-1225ye is added to the HFC-152a, indicating a minimum boiling azeotrope is formed.

Example 9

An ebulliometer, as described above, consisting of a vacuum jacketed tube with a condenser on top which is further equipped with a quartz thermometer is used. About 15 g HFC-152a is charged to the ebulliometer and then HFO-1225zc is added in small, measured increments. Temperature depression is observed when HFO-1225zc is added to the HFC-152a, indicating a minimum boiling azeotrope is formed. As shown in Table 4, from greater than about 0 to about 60 weight percent HFO-1225zc, the boiling point of the composition changed by less than 2° C.

TABLE 4

HFO-1225zc/HFC-152a compositions at 14.40 psia

| Wt. % HFC-152a | Wt. % HFO-1225zc | Temperature (° C.) |
|---|---|---|
| 100.00 | 0.00 | −22.68 |
| 97.41 | 2.59 | −22.92 |
| 91.70 | 8.30 | −23.36 |
| 85.16 | 14.84 | −23.96 |
| 72.61 | 27.39 | −24.28 |
| 64.34 | 35.66 | −24.38 |
| 59.48 | 40.52 | −24.40 |
| 53.81 | 46.19 | −24.38 |
| 47.82 | 52.18 | −24.31 |
| 44.63 | 55.37 | −24.28 |
| 43.46 | 56.64 | −24.20 |

Example 10

An ebulliometer, as described above, consisting of a vacuum jacketed tube with a condenser on top which is further equipped with a quartz thermometer is used. About 15 g HFC-152a is charged to the ebulliometer and then HFO-1225yc is added in small, measured increments. Temperature depression is observed when HFO-1225yc is added to the HFC-152a, indicating a minimum boiling azeotrope is formed.

Example 11

An ebulliometer, as described above, consisting of a vacuum jacketed tube with a condenser on top which is further equipped with a quartz thermometer is used. About 21 g Z-HFO-1225ye is charged to the ebulliometer and then HFO-1234ze is added in small, measured increments. Temperature depression is observed when HFO-1234ze is added to the Z-HFO-1225ye, indicating a minimum boiling azeotrope is formed. As shown in Table 5, from greater than about 50 to about 100 weight percent Z-HFO-1225ye, the boiling point of the composition changed by about 1° C. or less.

TABLE 5

Z-HFO-1225ye/HFO-1234ze compositions at 14.40 psia

| Wt. % Z-HFO-1225ye | Wt. % HFO-1234ze | Temperature (° C.) |
|---|---|---|
| 100.00 | 0.00 | −20.002 |
| 99.68 | 0.32 | −20.012 |
| 95.88 | 4.12 | −20.349 |
| 89.64 | 10.36 | −20.389 |
| 80.58 | 19.42 | −20.399 |
| 71.45 | 28.55 | −20.399 |
| 63.66 | 36.34 | −20.399 |
| 60.56 | 39.44 | −20.399 |
| 55.22 | 44.78 | −20.349 |
| 49.91 | 50.09 | −20.300 |

Example 12

An ebulliometer, as described above, consisting of a vacuum jacketed tube with a condenser on top which is further equipped with a quartz thermometer is used. About 21 g E-HFO-1225ye is charged to the ebulliometer and then HFO-1234ze is added in small, measured increments. Temperature depression is observed when HFO-1234ze is added to the E-HFO-1225ye, indicating a minimum boiling azeotrope is formed.

Example 13

An ebulliometer, as described above, consisting of a vacuum jacketed tube with a condenser on top which is further equipped with a quartz thermometer is used. About 21 g E/Z-HFO-1225ye is charged to the ebulliometer and then HFO-1234ze is added in small, measured increments. Temperature depression is observed when HFO-1234ze is added to the E/Z-HFO-1225ye, indicating a minimum boiling azeotrope is formed.

Example 14

An ebulliometer, as described above, consisting of a vacuum jacketed tube with a condenser on top which is further equipped with a quartz thermometer is used. About 21 g HFO-1225zc is charged to the ebulliometer and then HFO-1234ze is added in small, measured increments. Temperature depression is observed when HFO-1234ze is added to the HFO-1225zc, indicating a minimum boiling azeotrope is formed.

Example 15

An ebulliometer, as described above, consisting of a vacuum jacketed tube with a condenser on top which is further equipped with a quartz thermometer is used. About 21 g HFO-1225yc is charged to the ebulliometer and then HFO-1234ze is added in small, measured increments. Temperature depression is observed when HFO-1234ze is added to the HFO-1225yc, indicating a minimum boiling azeotrope is formed.

Examples 16–33

These examples show that the constant-boiling blends of the present invention have certain advantages when compared to other refrigerants which are currently used in certain refrigeration cycles.

The theoretical performance of a refrigerant at specific operating conditions can be estimated from the thermodynamic properties of the refrigerant using standard refrigeration cycle analysis techniques; see for example, R. C.

Downing, FLUOROCARBON REFRIGERANTS HANDBOOK, Chapter 3, Prentice-Hall, 1988. The coefficient of performance (COP) is a universally accepted measure, especially useful in representing the relative thermodynamic efficiency of a refrigerant in a specific heating or cooling cycle involving evaporation or condensation of the refrigerant. In refrigeration engineering, this term expresses the ratio of useful refrigeration to the energy applied by the compressor in compressing the vapor. The capacity of a refrigerant represents the amount of cooling or heating the refrigerant provides. To a compressor engineer, this value expresses the capability of a compressor to pump quantities of heat for a given volumetric flow rate of refrigerant. In other words, given a specific compressor, a refrigerant with a higher capacity will deliver more cooling or heating power.

This type of calculation is performed for a refrigeration/air conditioning cycle where the condenser temperature is typically 150° F. and the evaporator temperature is typically −35° F. It is further assumed that the following apply: isentropic compression and a compressor inlet temperature of 45° F. Such calculations are performed for various combinations of HFO-1225 and HFC-152a or HFO-1243zf. Tables 6 and 7 below list the COP and capacity of the various blends over a range of condenser and evaporator temperatures relative to 1,1,1,2-tetrafluoroethane (HFC-134a), a commonly-used, conventional refrigerant.

TABLE 6

| Example | Composition HFO-1225/HFC-152a (by weight) | COP | CAPACITY | DISCHARGE TEMPERATURE (° F.) |
|---|---|---|---|---|
| 16 | 90/10 | 0.98 | 0.70 | 252 |
| 17 | 80/20 | 0.98 | 0.83 | 255 |
| 18 | 70/30 | 0.99 | 0.88 | 258 |
| 19 | 60/40 | 1.00 | 0.99 | 262 |
| 20 | 50/40 | 1.02 | 0.98 | 266 |
| 21 | 40/50 | 1.03 | 0.97 | 270 |
| 22 | 30/70 | 1.02 | 0.96 | 275 |
| 23 | 20/80 | 1.01 | 0.95 | 280 |
| 24 | 10/90 | 1.01 | 0.94 | 285 |

TABLE 7

| Example | Composition HFO-1225/HFO- | COP | CAPACITY | DISCHARGE TEMPERATURE (° F.) |
|---|---|---|---|---|
| 25 | 90/10 | 0.98 | 0.72 | 251 |
| 26 | 80/20 | 0.98 | 0.84 | 252 |
| 27 | 70/30 | 0.99 | 0.88 | 253 |
| 28 | 60/40 | 1.00 | 0.99 | 264 |
| 29 | 50/40 | 1.02 | 1.02 | 265 |
| 30 | 40/50 | 1.03 | 0.99 | 267 |
| 31 | 30/70 | 1.02 | 0.97 | 268 |
| 32 | 20/80 | 1.01 | 0.95 | 269 |
| 33 | 10/90 | 1.01 | 0.94 | 272 |

What is claimed is:

1. An azeotrope-like composition comprising from greater than zero to about 99 wt. % of HFO-1225 and from about 1 wt. % to less than 100 wt. % of a fluid selected from the group consisting of HFO-1243zf, HFC-152a, HFO-1234ze, and combinations of two or more thereof.

2. The azeotrope-like composition of claim 1 comprising from greater than zero to about 75 wt. % of HFO-1225 and from about 25 wt. % to less than 100 wt. % of the fluid selected from the group consisting of HFO-1243zf, HFC-152a, HFO-1234ze, and combinations of two or more thereof.

3. The azeotrope-like composition of claim 1 comprising from about 5 wt. % to about 90 wt. % of HFO-1225 and from about 10 wt. % to about 90 wt. % of the fluid selected from the group consisting of HFO-1243zf, HFC-152a, HFO-1234ze, and combinations of two or more thereof.

4. The azeotrope-like composition of claim 1 wherein said azeotrope-like composition has a boiling point of from about −18° C. to about −28° C. at about 14 psia.

5. The azeotrope-like composition of claim 1 wherein said azeotrope-like composition has a boiling point of about −22° C. to about −28° C. at about 14 psia.

6. The azeotrope-like composition of claim 1 wherein said azeotrope-like composition has a boiling point of about −21° C. to about −26° C. at about 14 psia.

7. The azeotrope-like composition of claim 4 wherein said azeotrope-like composition has a boiling point of about −20° C.±2° C. at about 14 psia.

8. The azeotrope-like composition of claim 5 comprising from greater than zero to about 50 wt. % of HFO-1225 and from about 50 wt. % to less than 100 wt. % of HFO-1243zf.

9. The azeotrope-like composition of claim 8 comprising from greater than zero to about 25 wt. % of HFO-1225 and from about 75 wt. % to less than 100 wt. % of HFO-1243zf.

10. The azeotrope-like composition of claim 9 comprising from about 1 wt. % to about 20 wt. % of HFO-1225 and from about 80 wt. % to about 99 wt. % of HFO-1243zf.

11. The azeotrope-like composition of claim 8 wherein said azeotrope-like composition has a boiling point of about −24° C. to about −28° C. at about 14.4 psia.

12. The azeotrope-like composition of claim 8 wherein said azeotrope-like composition has a boiling point of about −23° C. to about −27° C. at about 14 psia.

13. The azeotrope-like composition of claim 11 comprising from greater than zero to about 50 wt. % of HFO-1225ye and from about 50 wt. % to less than 100 wt. % of HFO-1243zf.

14. The azeotrope-like composition of claim 13 comprising from greater than zero to about 25 wt. % of HFO-1225ye and from about 75 wt. % to less than 100 wt. % of HFO-1243zf.

15. The azeotrope-like composition of claim 14 comprising from about 1 to about 20 wt. % of HFO-1225ye and from about 80 wt. % to about 99 wt. % of HFO-1243zf.

16. The azeotrope-like composition of claim 15 comprising from about 1 to about 15 wt. % of HFO-1225ye and from about 85 wt. % to about 99 wt. % of HFO-1243zf.

17. The azeotrope-like composition of claim 13 wherein said HFO-1225ye comprises Z-HFO-1225ye.

18. The azeotrope-like composition of claim 15 wherein said HFO-1225ye comprises Z-HFO-1225ye.

19. The azeotrope-like composition of claim 18 wherein said azeotrope-like composition has a boiling point of about −26° C. to about −28° C. at about 14.4 psia.

20. The azeotrope-like composition of claim 13 wherein said HFO-1225ye comprises E-HFO-1225ye.

21. The azeotrope-like composition of claim 15 wherein said HFO-1225ye comprises E-HFO-1225ye.

22. The azeotrope-like composition of claim 21 wherein said azeotrope-like composition has a boiling point of about −26° C. to about −28° C. at about 14.4 psia.

23. The azeotrope-like composition of claim 13 wherein said HFO-1225ye comprises E/Z-HFO-1225ye.

24. The azeotrope-like composition of claim 15 wherein said HFO-1225ye comprises E/Z-HFO-1225ye.

25. The azeotrope-like composition of claim 24 wherein said azeotrope-like composition has a boiling point of about −26° C. to about −28° C. at about 14.4 psia.

26. The azeotrope-like composition of claim 12 comprising from greater than zero to about 50 wt. % of HFO-1225zc and from about 50 wt. % to less than 100 wt. % of HFO-1243zf.

27. The azeotrope-like composition of claim 26 comprising from greater than zero to about 40 wt. % of HFO-1225zc and from about 60 wt. % to less than 100 wt. % of HFO-1243zf.

28. The azeotrope-like composition of claim 27 comprising from about 1 to about 20 wt. % of HFO-1225zc and from about 80 wt. % to about 99 wt. % of HFO-1243zf.

29. The azeotrope-like composition of claim 28 wherein said azeotrope-like composition has a boiling point of about −24° C. to about −26° C. at about 14 psia.

30. The azeotrope-like composition of claim 6 comprising from greater than zero to about 99 wt. % of HFO-1225 and from about 1 wt. % to less than 100 wt. % of HFC-152a.

31. The azeotrope-like composition of claim 30 comprising from greater than zero to about 75 wt. % of HFO-1225 and from about 25 wt. % to less than 100 wt. % of HFC-152a.

32. The azeotrope-like composition of claim 31 comprising from about 1 wt. % to about 20 wt. % of HFO-1225 and from about 80 wt. % to about 99 wt. % of HFC-152a.

33. The azeotrope-like composition of claim 30 wherein said azeotrope-like composition has a boiling point of about −23° C.±2° C. at about 14 psia.

34. The azeotrope-like composition of claim 33 comprising from greater than zero to about 75 wt. % of HFO-1225ye and from about 25 wt. % to less than 100 wt. % of HFC-152a.

35. The azeotrope-like composition of claim 34 comprising from greater than zero to about 60 wt. % of HFO-1225ye and from about 40 wt. % to less than 100 wt. % of HFC-152a.

36. The azeotrope-like composition of claim 35 comprising from greater than zero to about 40 wt. % of HFO-1225ye and from about 60 wt. % to less than 100 wt. % of HFC-152a.

37. The azeotrope-like composition of claim 36 comprising from about 1 to about 25 wt. % of HFO-1225ye and from about 75 wt. % to about 99 wt. % of HFC-152a.

38. The azeotrope-like composition of claim 34 wherein said HFO-1225ye comprises Z-HFO-1225ye.

39. The azeotrope-like composition of claim 36 wherein said HFO-1225ye comprises Z-HFO-1225ye.

40. The azeotrope-like composition of claim 39 wherein said azeotrope-like composition has a boiling point of about −23° C.±2° C. at about 14 psia.

41. The azeotrope-like composition of claim 34 wherein said HFO-1225ye comprises E-HFO-1225ye.

42. The azeotrope-like composition of claim 36 wherein said HFO-1225ye comprises E-HFO-1225ye.

43. The azeotrope-like composition of claim 42 wherein said azeotrope-like composition has a boiling point of about −23° C.±2° C. at about 14 psia.

44. The azeotrope-like composition of claim 34 wherein said HFO-1225ye comprises E/Z-HFO-1225ye.

45. The azeotrope-like composition of claim 36 wherein said HFO-1225ye comprises E/Z-HFO-1225ye.

46. The azeotrope-like composition of claim 45 wherein said azeotrope-like composition has a boiling point of about −26° C. to about −28° C. at about 14.4 psia.

47. The azeotrope-like composition of claim 30 wherein said azeotrope-like composition has a boiling point of about −24° C.±2° C. at about 14 psia.

48. The azeotrope-like composition of claim 47 comprising from about 10 wt. % to about 99 wt. % of HFO-1225zc and from about 1 wt. % to about 90 wt. % of HFC-152a.

49. The azeotrope-like composition of claim 48 comprising from about 10 wt. % to about 60 wt. % of HFO-1225zc and from about 40 wt. % to about 90 wt. % of HFC-152a.

50. The azeotrope-like composition of claim 49 comprising from about 10 wt. % to about 50 wt. % of HFO-1225zc and from about 50 wt. % to about 90 wt. % of HFC-152a.

51. The azeotrope-like composition of claim 7 comprising from about 1 wt. % to about 99 wt. % of HFO-1225 and from about 1 wt. % to about 99 wt. % of HFO-1234ze.

52. The azeotrope-like composition of claim 51 comprising from about 25 wt. % to about 99 wt. % of HFO-1225 and from about 1 wt. % to about 75 wt. % of HFO-1234ze.

53. The azeotrope-like composition of claim 52 comprising from about 50 wt. % to about 90 wt. % of HFO-1225 and from about 10 wt. % to about 50 wt. % of HFO-1234ze.

54. The azeotrope-like composition of claim 51 wherein said HFO-1225 is HFO-1225ye.

55. The azeotrope-like composition of claim 54 wherein said HFO-1225ye comprises Z-HFO-1225ye.

56. The azeotrope-like composition of claim 54 wherein said HFO-1225ye comprises E-HFO-1225ye.

57. The azeotrope-like composition of claim 54 wherein said HFO-1225ye comprises E/Z-HFO-1225ye.

58. The azeotrope-like composition of claim 1 wherein said HFO-1225 is HFO-1225yc.

59. A refrigerant composition comprising an azeotrope-like composition of claim 1.

60. A refrigeration system comprising a refrigerant of claim 59.

61. A method for cooling an article which comprises evaporating a refrigerant composition of claim 57 in the vicinity of the article to be cooled.

62. A method for heating an article which comprises condensing a refrigerant composition of claim 59 in the vicinity of the article to be heated.

63. A sprayable composition comprising a material to be sprayed and a propellant comprising an azeotrope-like composition of claim 1.

64. A blowing agent comprising an azeotrope-like composition of claim 1.

65. A closed cell foam prepared by foaming a foamable composition in the presence of a blowing agent comprising the azeotrope-like composition of claim 1.

66. The closed cell foam of claim 65 wherein said foamble composition comprises polyurethane, polyisocyanurate, polystyrene, polyethylene, and mixtures thereof.

67. A method of reducing the flammability of a fluid comprising adding an azeotrope-like composition of claim 1 to said fluid.

68. A method of suppressing a flame comprising contacting said flame with a fluid comprising an azeotrope-like composition of claim 1.

69. A method of sterilizing an article, said method comprising contacting said article to be sterilized with a composition comprising an azeotrope-like composition of claim 1.

70. The method of claim 69 wherein said composition further comprises ethylene oxide.

71. A method of forming a foam comprising adding to a foamable composition a blowing agent comprising an azeotrope-like composition of claim 1.

72. A premix of a polyol and a blowing agent wherein the blowing agent comprises an azeotrope-like composition of claim 1.

* * * * *